United States Patent [19]

Ohtake et al.

[11] 4,314,029
[45] Feb. 2, 1982

[54] APPARATUS FOR AUTOMATICALLY MEASURING CHANGES IN AMOUNT OF GAS

[75] Inventors: Yukio Ohtake; Masahiro Nakamura, both of Tokyo, Japan

[73] Assignee: Ohtake Works Company, Ltd., Tokyo, Japan

[21] Appl. No.: 117,736

[22] Filed: Feb. 1, 1980

[30] Foreign Application Priority Data

Feb. 7, 1979 [JP] Japan .................. 54-12283

[51] Int. Cl.³ ............................................. C12M 1/34
[52] U.S. Cl. .................... 435/291; 422/102; 435/807; 435/808; 435/817
[58] Field of Search ............. 435/291, 34, 39, 40, 435/807, 808, 817; 422/57, 61, 102; 23/230 B

[56] References Cited

U.S. PATENT DOCUMENTS

| | | | |
|---|---|---|---|
| 1,046,259 | 12/1912 | Bunzel | 4435/291 X |
| 2,019,950 | 11/1935 | Bunzell | 435/291 X |
| 3,322,956 | 5/1967 | Shah | 435/291 X |
| 3,403,081 | 9/1968 | Rohrback et al. | 435/291 X |
| 3,421,982 | 1/1969 | Schultz et al. | 435/291 X |
| 3,635,681 | 1/1972 | Rogers | 435/291 X |
| 3,890,201 | 6/1975 | Cady | 435/291 |
| 3,907,646 | 9/1975 | Wilkins et al. | 435/291 |
| 3,950,227 | 4/1976 | Efthymiou | 435/291 X |

Primary Examiner—Robert J. Warden
Attorney, Agent, or Firm—Jordan and Hamburg

[57] ABSTRACT

Apparatus for automatically measuring changes in amount of gas comprises a pressure sensor being attached to a closed vessel having a main chamber in which is contained a liquid enzyme or the like and adapted to convert a change in pressure within said vessel into an electric signal and output a measured pressure value signal; a photoelectric sensor adapted to convert an optical change of the liquid enzyme or the like within said closed vessel into an electric signal and output an optical measured value signal; an electrode adapted to come into contact with the liquid enzyme or the like within the vessel to convert a change in conductivity into an electric signal and output a measured conductivity signal; and an arithmetic circuit adapted to input respectively said measured pressure value signal, the measured pressure value signal and said optical measured value signal, and the measured pressure value signal and said measured conductivity signal simultaneously, effect calculations simultaneously in parallel according to a predetermined numerical expression stored in advance and output respective calculation data signals.

10 Claims, 8 Drawing Figures

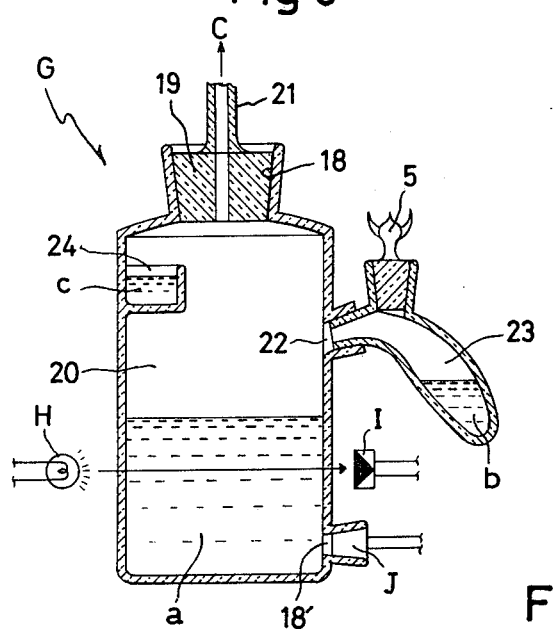
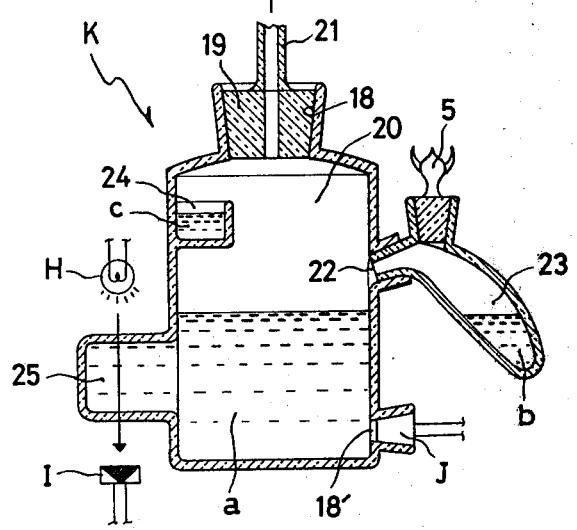

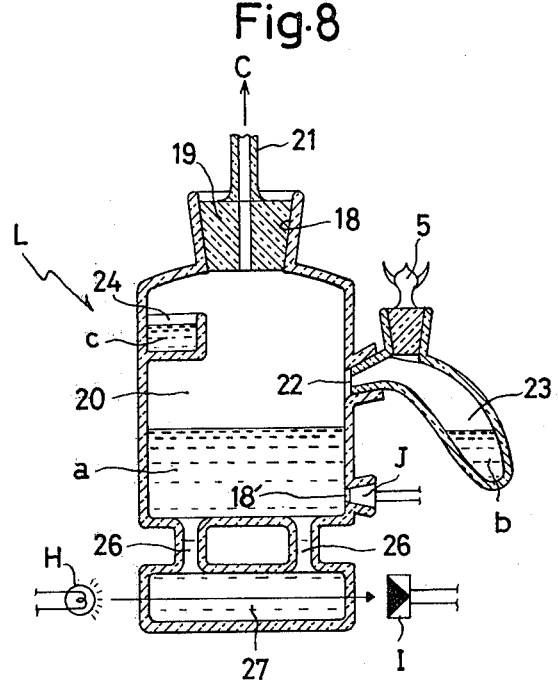

APPARATUS FOR AUTOMATICALLY MEASURING CHANGES IN AMOUNT OF GAS

This invention relates to an apparatus for automatically measuring changes in amount of gas within a closed vessel used for measuring the photosynthesis of plants, etc. and for studying the activity, tissue metabolism, etc. of many enzymes contained in animals, plants and microorganisms.

Heretofore, the change in amount of gas within a closed vessel has generally been measured by such a Warburg's manometer Z as shown in FIG. 1. For example, the activity condition of many enzymes contained in animals, plants and microorganisms can be checked by the exchange of gas resulting from respiration or glycolysis, that is, the consumption of oxygen and evolving of carbon dioxide. The change in amount of gas is measured under constant temperature and volume by the Warburg's manometer shown in FIG. 1. In general, the change in amount of oxygen (partial pressure of oxygen) rather than carbon dioxide is measured.

The Warburg's manometer Z comprises an Erlenmeyer flask type vessel A and a Warburg's manometer B. The vessel A has a main chamber 1 into which is added a liquid enzyme, a, a side chamber 2 into which is added a liquid substrate, b, and further a subchamber 3 into which is added an absorbent, c, (a filter paper impregnated with a sodium hydroxide solution) for absorbing carbon dioxide produced during reaction.

The vessel A is immersed in a thermostatic water tank (not shown), then a three-way cock 4 and a gas exchanging tube plug 5 are closed and the manometer is tilted to allow the liquid substrate, b, in the side chamber 2 to incorporate into the main chamber 1 followed by shaking. As a result, oxygen is absorbed by the liquid enzyme, a, and carbon dioxide evolved is absorbed by the absorbent, c, and as the amount of gas within the main chamber 1 of the vessel A there appears only a change (reduction) in amount of oxygen. This change is read, through a conduit 6, as a pressure difference, h(mm), between the inner pressure of the Warburg's manometer B and the atmospheric pressure. If a predetermined vessel constant is k(mm$^2$), the change in amount of gas, x (mm$^3 = \mu$l, 0° C., 760 mmHg), is calculated as x = h·k. This method has long been widely applied for measuring the respiration velocity of mitochondria and cell dispersions, tissue homogenate and tissue slice. In this Warburg's manometer Z, however, one end of a U-shaped glass tube is open to the atmosphere, so it is very sensitive to only a slight change in atmospheric pressure and is therefore influenced by a change in atmospheric pressure arising during measurement, and even a slight change in temperature of the thermostatic water tank affects reading. It is therefore necessary to make correction for measured values. For this reason, it has not only been impossible to obtain continuous measured values, but also been difficult to effect automatic observation and recording with the lapse of time.

There has also been known an optical measurement in which light is passed through the solution, a, within the main chamber 1 of the closed vessel A and the absorbance or scattered light is detected by a phototube or the like, or the use of an electrode in which the detection end is directly immersed in the solution, a, and the concentration of dissolved oxygen is measured with the lapse of time. The former optical measurement effects absorbance analysis, namely the analysis of absorption spectrum of solution, in which according to the concentration of dissolved oxygen a specific wavelength region is absorbed or scattered to cause its spectrum or luminous intensity to become changed, and this change is sensed by a phototube and converted to an electric signal, whereby the analysis of the solution, a, within the closed vessel A can be made and indirectly the change in amount of gas can also be measured. On the other hand, in the latter method of using an electrode, the electrode is hung and immersed directly into the solution, a, then electricity is fed, and according to the concentration of dissolved oxygen in the solution, a, the change in conductivity or in electric resistance is measured whereby the concentration of oxygen in the solution, a, and the change in amount of gas within the closed vessel A can be known.

In the two methods mentioned above, measured values are detected as electric signals, so it is possible to effect automatic observation and recording.

In these two methods, however, the gas within the enclosed vessel is not directly measured, so observation is made in combination with the foregoing Warburg's method. But, since the Warburg's manometer Z uses a U-shaped glass tube, it is basically impossible to obtain electrical measured values, which impedes automatic measurement of this equipment; besides, since the difference in height of the liquid in the two legs of the U-shaped glass tube indicates the pressure, there easily occur errors and mistakes, and ample care must be exercised for the handling. In addition, the long and large size of the manometer itself affects the other attachments (shaking device, thermostatic water tank, etc.), requiring a larger scale of the entire equipment. Thus, various drawbacks are encountered in such conventional methods.

It is an object of this invention to provide an apparatus for automatically measuring changes in amount of gas which apparatus solves the aforesaid many problems and is simplified in construction and automated to make continuous observation and recording with the lapse of time possible.

Other objects of this invention will become apparent by referring to this specification and the accompanying drawings, in which:

FIG. 1 typifies the conventional Warburg's manometer;

FIGS. 6 through 8 are central longitudinal sections respectively of first through third embodiments of a closed vessel in the apparatus Y of this invention.

Figure 2:
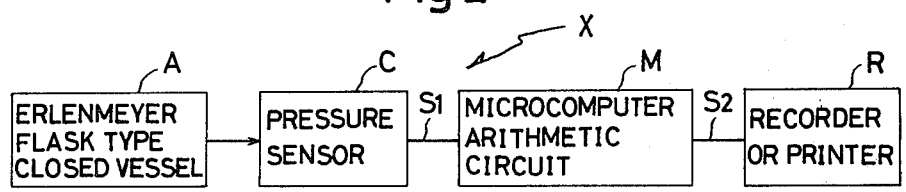
FIGS. 2 and 3 are block diagrams respectively showing the construction of apparatus X and Y for automatically measuring changes in amount of gas according to this invention.

An embodiment of this invention is described below with reference to FIGS. 2 and 4.

Figure 1:
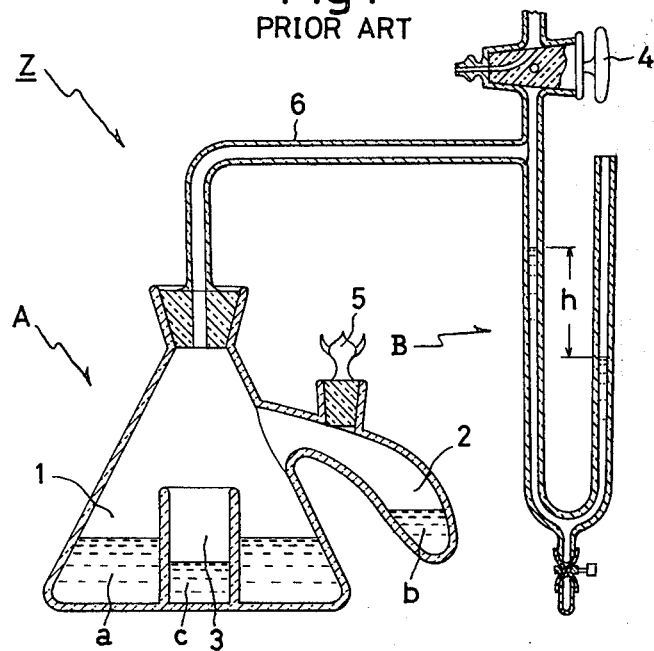
Figure 4:
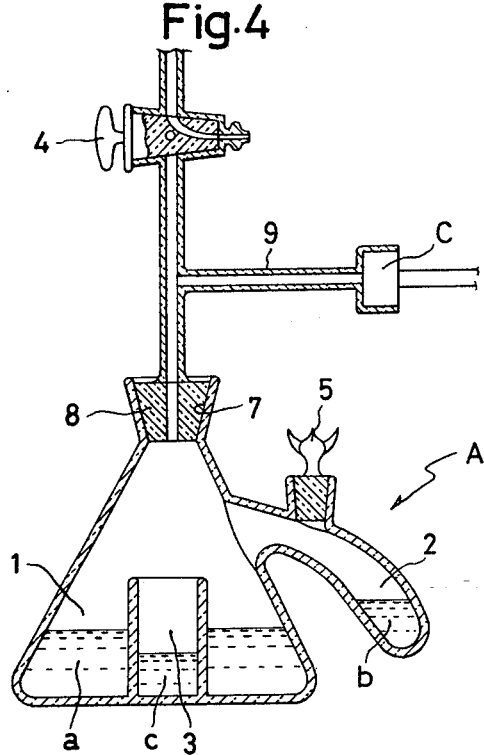
FIGS. 4 and 5 are central longitudinal sections respectively of first and second embodiments of a closed vessel in the apparatus X of this invention.

An apparatus for automatically measuring changes in amount of gas, X, according to this invention, as illustrated in FIG. 4, includes an Erlenmeyer flask type vessel A and a pressure sensor C, which vessel A is the same as that of the Warburg's manometer Z shown in FIG. 1, the pressure sensor C replacing the manometer B. As illustrated in FIG. 2, the change in amount of gas within the Erlenmeyer flask type vessel A is measured by the pressure sensor C attached to a horizontal end of a λ-shaped conduit 9 which is mounted upright on a cap 8 which fits tightly in a vessel mouth 7, the conduit 9 communicating with the main chamber 1, and a measured pressured value signal, s1, is fed to a microcomputer arithmetic circuit, M, which pre-stores a predetermined numerical expression, and a calculation data signal, s2, is recorded by a recorder or printer, R. This invention constructed as above employs quite the same principle as that of the conventional Warburg's manometer Z and can be used for the measurement, inspection and study of changes in amount of gas.

Figure 5:
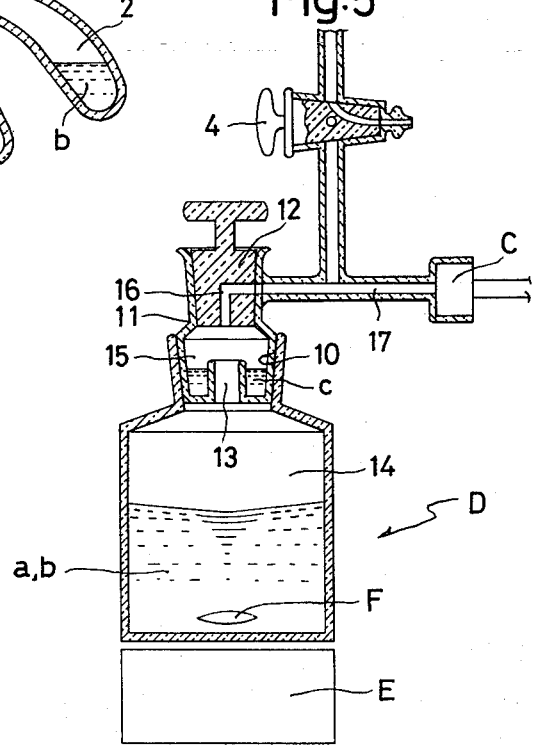

FIG. 5 shows a second embodiment of the apparatus X of this invention, in which a cylindrical vessel D is used in place of the Erlenmeyer flask type vessel A shown in FIG. 4. This embodiment is used mainly for the measurement of BOD (biochemical oxygen demand)(ppm), in which a vessel mouth 10 is in a largely opened shape since a stirrer blade F is placed in the cylindrical vessel D, and a cap 11 which fits in the vessel port 10 is shaped so that in the upper half part thereof there tightly fits a cock 12 and in the lower half part there is formed internally about a through hole 13 an annular subchamber 15 for communication with the main chamber 14. And the gas within the closed vessel D is conducted to the pressure sensor C attached to a horizontal end of an inverted T-shaped conduit 17, the conduit 17 being secured to one side of the cap 11 for communication with the main chamber through the through hole 13 and a right-angled hole 16 formed in the cock 12.

The cylindrical vessel D is not provided with a portion corresponding to the side chamber 2 in FIG. 4, but for pouring the liquid enzyme, a, and further the liquid substrate, b, into the vessel D, the cap 11 is pulled out. In this case, the stirrer blade F may be placed beforehand in the main chamber 14 of the vessel D. Then the absorbent, c, is put into the subchamber 15 formed in the cap 11 and the cap 11 is set. Now, preparations are over.

The stirrer blade F is given a turning effort by the magnetic stirrer E which is mounted in close proximity to the outer bottom surface of the vessel D; the cock 12 is turned to align the right-angled hole 16 with the conduit 17 to conduct gas into the pressure sensor C. By this operation procedure, it becomes possible to automatically record continuous data of higher accuracy than in the BOD measurement by the conventional Warburg's method.

Another embodiment of this invention is described below with reference to FIGS. 3 and 6.

In an apparatus Y according to this invention, a λ-shaped conduit 21 (only partly shown) is mounted upright on a cap 19 which fits in a vessel mouth 18 of a cylindrical vessel G, the conduit 21 communicating with a main chamber 20, and to a horizontal end of the conduit 21 is attached the pressure sensor C; in addition, there are provided a projector H for absorbance analysis and a photo detector (phototube) I as a photoelectric sensor, further provided is an electrode J mounted through an electrode opening 18' formed on one side of the bottom portion, whereby it is intended to obtain three kinds of data from one vessel G. In the main chamber 20 of the cylindrical vessel G is placed the liquid enzyme, a, and the liquid substrate, b, is charged into a side chamber 23 which is removably attached to a mounting port 22 open at an upper portion of one side of the vessel G, the side chamber 23 being communicatable with the main chamber 20, and further the absorbent, c, is put in a subchamber 24 formed in a shelf fashion on the upper inner surface of the other side of the vessel.

The vessel G is tilted to allow the liquid substrate, b, in the side chamber 23 to be poured into the main chamber 20 followed by shaking while measurement is started.

Figure 3:
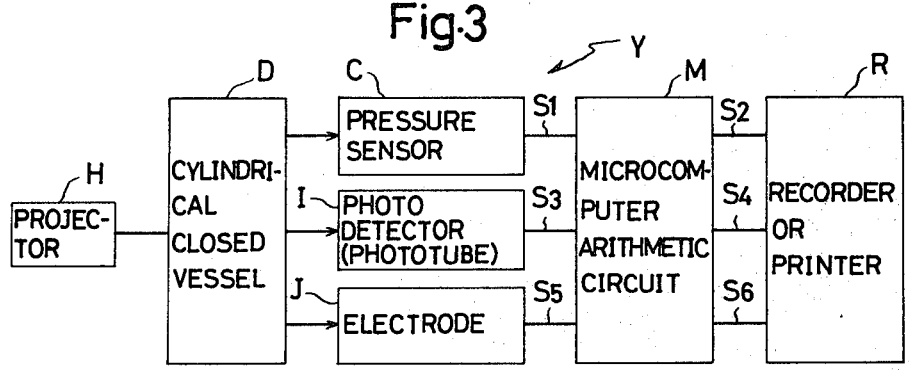

In the apparatus Y of this invention constructed as above, as is illustrated in FIG. 3, the pressure of the gas within the cylindrical vessel G is measured by the pressure sensor C through the conduit 21 and a measured pressure value signal, s1, is fed to the microcomputer arithmetic circuit M, then a calculation data signal, s2, is recorded by a recorder or printer; at the same time, light is radiated from the projector H through the solution, a, within the closed vessel G and the photo detector I mounted on the opposite side measures and converts the state of the solution, a, into an electric signal and delivers an optical measured value signal, s3, to the microcomputer arithmetic circuit M, then a calculation data signal, s4, is recorded by the recorder or printer R. Further, to measure the concentration of oxygen dissolved in the closed vessel G, electricity is fed to the solution, a, by means of the electrode J mounted at the lower portion of the vessel G, whereby an electric resistance is measured conductivity signal, s5, is obtained. And a calculation data signal, s6, resulting from processing in the microcomputer arithmetic circuit M is recorded with the lapse of time by the recorder or printer R. Thus, a desired observation and experiment can be effected entirely automatically.

FIG. 7 shows a second embodiment of the apparatus Y of this invention, in which a cylindrical closed vessel K is provided with an optical measuring compartment 25 for communication with the main chamber 20, the compartment 25 projecting outward on the other side of the bottom portion of the vessel G in FIG. 6, whereby it is intended to facilitate measurement.

Furthermore, FIG. 8 shows a third embodiment of the apparatus Y of this invention, in which for optical measurement a cylindrical closed vessel L is provided specially with an optical measuring annexed chamber 27 through the medium of through holes 26, 26 formed in the outer bottom surface of the vessel G in FIG. 6, whereby it is also intended to facilitate measurement.

The apparatus X and Y for automatically measuring change in amount of gas within a closed vessel constructed as above according to this invention do not change the principle of measurement of the conventional Warburg's method using manometer, but realize the simplification and automation of such measuring apparatus and remedy the drawback of the Warburg's method that it has been impossible to make continuous observation with the lapse of time; furthermore, by the introduction of a microcomputer capable of effecting calculations according to predetermined numerical expressions and processing data automatically for a long time, it becomes possible to obtain data promptly and accurately.

Moreover, the apparatus Y for automatically measuring changes in amount of gas according to this invention permits the application of optical absorbance analysis and electrode method, whereby analysis from every angle is made possible.

What is claimed is:

1. Apparatus for automatically measuring changes in oxygen absorption during material activity such as changes in enzyme activity, photosynthesis of plants, and biochemical oxygen demand, comprising a closed vessel means having a main chamber in which an activity material whose activity is to be measured is contained, said vessel also having a subchamber in which a liquid substrate is contained, a shelf provided on the upper inner surface of said vessel means for housing an absorbent, a pressure sensing means attached to said closed vessel means for converting a change in oxygen partial pressure within said vessel means into an electric signal and outputting a measured oxygen partial pressure value signal, and an arithmetic circuit means for effecting calculation according to a predetermined numerical expression stored in advance after inputting said measured oxygen partial pressure value signal and for outputting a calculation data signal.

2. Apparatus according to claim 1, in which said closed vessel means is an Erlenmeyer flask-type vessel means which is provided exteriorly of one side thereof with said subchamber for housing therein said liquid substrate, communicating means communicating said subchamber with said main chamber.

3. Apparatus according to claim 1, in which said pressure sensing means is attached to said closed vessel means through the means of a conduit means, a cap means on said vessel means, said conduit means being attached to said cap means which tightly fits in a mouth of said vessel means.

4. Apparatus for automatically measuring changes in oxygen absorption during material activity such as changes in enzyme activity, photosynthesis of plants, and biochemical oxygen demand, comprising a closed vessel means having a main chamber in which an activity material whose activity is to be measured is contained, said vessel also having a subchamber in which a liquid substrate is contained, a shelf provided on the upper inner surface of said vessel means for housing an absorbent, a pressure sensing means attached to said closed vessel means for converting a change in oxygen partial pressure within said vessel means into an electric signal and outputting a measured oxygen partial pressure signal, a photoelectric sensing means for converting an optical change of said activity material within said closed vessel means into an electric signal and outputting an optical measured value signal, an electrode means adapted to come into contact with the activity material within said vessel means for converting a change in conductivity of said activity material into an electric signal and outputting a measured conductivity signal, and an arithmetic circuit means simultaneously effecting calculations in parallel according to a predetermined numerical expression stored in advance after simultaneously inputting said measured oxygen partial pressure value signal, said optical measured value signal and said measured conductivity signal simultaneously and for outputting respective calculation data signals.

5. Apparatus according to claim 4, in which said closed vessel means is a cylindrical vessel provided exteriorly of one side thereof with said subchamber for containing therein said liquid substrate, means providing communication between said subchamber and said main chamber, and an optical measuring annexed chamber means at an outer bottom surface of said main chamber means and communicating with said main chamber.

6. Apparatus according to claim 4, in which said closed vessel means is a cylindrical vessel means which is provided exteriorly of one side thereof with said subchamber for housing therein said liquid substrate, means providing communication between said subchamber and said main chamber, and an optical measuring compartment means provided on the other side near the bottom of said vessel means and which communicates with said main chamber and which projects outwardly from said main chamber.

7. Apparatus according to claim 4, in which said closed vessel means is provided exteriorly of one side thereof with said subchamber for housing therein said liquid substrate, means providing communication between said subchamber and said main chamber, said electrode means being attached to one side of a bottom portion of said closed vessel means.

8. Apparatus according to claim 4, in which a cap means tightly fits in the mouth of said vessel means, said pressure sensing means being attached to said closed vessel means through the means of a conduit means, said conduit means being attached to said cap means.

9. Apparatus for automatically measuring changes in oxygen absorption during material activity such as changes in oxygen absorption during enzyme activity, photosynthesis of plants, and biochemical oxygen demand, comprising a closed vessel means having a main chamber in which an activity material whose activity is to be measured is contained, said vessel also having a subchamber in which a liquid substrate is contained, means providing communication between said subchamber and said main chamber so that said liquid substrate is transferrable from said subchamber to said main chamber without impairing the closed integrity of said closed vessel means, said transfer of said liquid substrate from said subchamber to said main chamber being effected when said measuring is to be commenced, a shelf means in said vessel which is separated from said activity material in said main chamber, absorbent means in said shelf for absorbing $CO_2$ released during said activity material, a pressure sensing means attached to said closed vessel means for converting a change in oxygen partial pressure within said vessel means into an electric signal and outputting a measured oxygen partial pressure value signal, a photoelectric sensing means for converting an optical change of said activity material within said closed vessel means into an electric signal and outputting an optical measured value signal, an electrode means adapted to come into contact with said activity material within said vessel means for converting a change in conductivity of said activity material into an electric signal and outputting a measured conductivity signal, and an arithmetic circuit means simultaneously effecting calculations in parallel according to a predetermined numerical expression stored in advance after simultaneously inputting said measured oxygen partial pressure value signal, said optical measured value signal and said measured conductivity signal simultaneously and for outputting respective calculation data signals, whereby the oxygen absorption of said activity material is measured by independently measuring the pressure, the luminous intensity, and the electrical conducting characteristics of said activity material such that the overall dependability of the automatic measuring apparatus is enhanced.

10. Apparatus for automatically measuring changes in oxygen absorption during material activity such as changes in enzyme activity, photosynthesis of plants, and biochemical oxygen demand, comprising a closed vessel means provided with a cap means, subchamber means containing an absorbent, said subchamber means being formed internally about a through hole in the lower part of said cap means for communication with said main chamber, a stirrer blade means in the main chamber to stir the material in the main chamber, a magnetic stirrer means mounted in close proximity to the outer bottom surface of said vessel means to operate said blade means, a pressure sensing means attached to said closed vessel means for converting a change in oxygen partial pressure within said vessel means into an electric signal and outputting a measured oxygen partial pressure valve signal, and an arithmetic circuit means for effecting calculation according to a predetermined numerical expression stored in advance after inputting said measured oxygen partial pressure valve signal and for outputting a calculation data signal.

* * * * *